US010850211B2

(12) United States Patent
Uthemann et al.

(10) Patent No.: US 10,850,211 B2
(45) Date of Patent: Dec. 1, 2020

(54) MICROFLUIDIC PROCESS WATER ANALYZER

(71) Applicant: HACH LANGE GMBH, Berlin (DE)

(72) Inventors: Rolf Uthemann, Solingen (DE); Markus Lenhard, Viersen (DE)

(73) Assignee: HACH LANGE GMBH, Berlin (DE)

( * ) Notice: Subject to any disclaimer, the term of this patent is extended or adjusted under 35 U.S.C. 154(b) by 0 days.

(21) Appl. No.: 16/314,660

(22) PCT Filed: Jul. 1, 2016

(86) PCT No.: PCT/EP2016/065549
§ 371 (c)(1),
(2) Date: Dec. 31, 2018

(87) PCT Pub. No.: WO2018/001520
PCT Pub. Date: Jan. 4, 2018

(65) Prior Publication Data
US 2019/0151768 A1    May 23, 2019

(51) Int. Cl.
*B01D 3/34* (2006.01)
*G01N 21/85* (2006.01)
(Continued)

(52) U.S. Cl.
CPC .............. *B01D 3/346* (2013.01); *B01D 1/14* (2013.01); *B01L 3/00* (2013.01); *C02F 1/048* (2013.01);
(Continued)

(58) Field of Classification Search
CPC .. B01D 1/14; B01D 3/00; B01D 3/346; C02F 1/048; G01N 21/8507; G01N 31/22
See application file for complete search history.

(56) References Cited

U.S. PATENT DOCUMENTS

| 4,724,044 A | 2/1988 | Weishaar et al. |
| 4,767,498 A | 8/1988 | Kreisler |

(Continued)

FOREIGN PATENT DOCUMENTS

| EP | 0315373 | 5/1989 |
| EP | 0504647 | 9/1992 |
| EP | 2290354 | 3/2011 |

OTHER PUBLICATIONS

International Search Report, dated Mar. 2, 2017, pp. 4.
International Searching Authority, Written Opinion of the International Searching Authority, dated Mar. 2, 2017, pp. 6.

*Primary Examiner* — Jonathan Miller
(74) *Attorney, Agent, or Firm* — Ference & Associates LLC

(57) ABSTRACT

The invention refers to a microfluidic process water analyzer (10) comprising an analyzer sample inlet (52), an optical sensor unit (40) for determination of an optical parameter of a liquid sample, a reagent tank (20; 201, 202, 203) being arranged fluidically upstream of the optical sensor unit (40) and comprising a liquid reagent (21), a waste tank (30; 301, 302, 303) arranged fluidically downstream of the optical sensor unit (40), an evaporation arrangement (32) comprising an evaporation chamber (33) arranged fluidically downstream of the optical sensor unit (40), the evaporation chamber (33) being actively vented with a drying gas pumped from a gas source (60) to the evaporation chamber (33). The evaporation arrangement allows to significantly reduce the volume of waste liquid.

15 Claims, 4 Drawing Sheets

Figure 1:
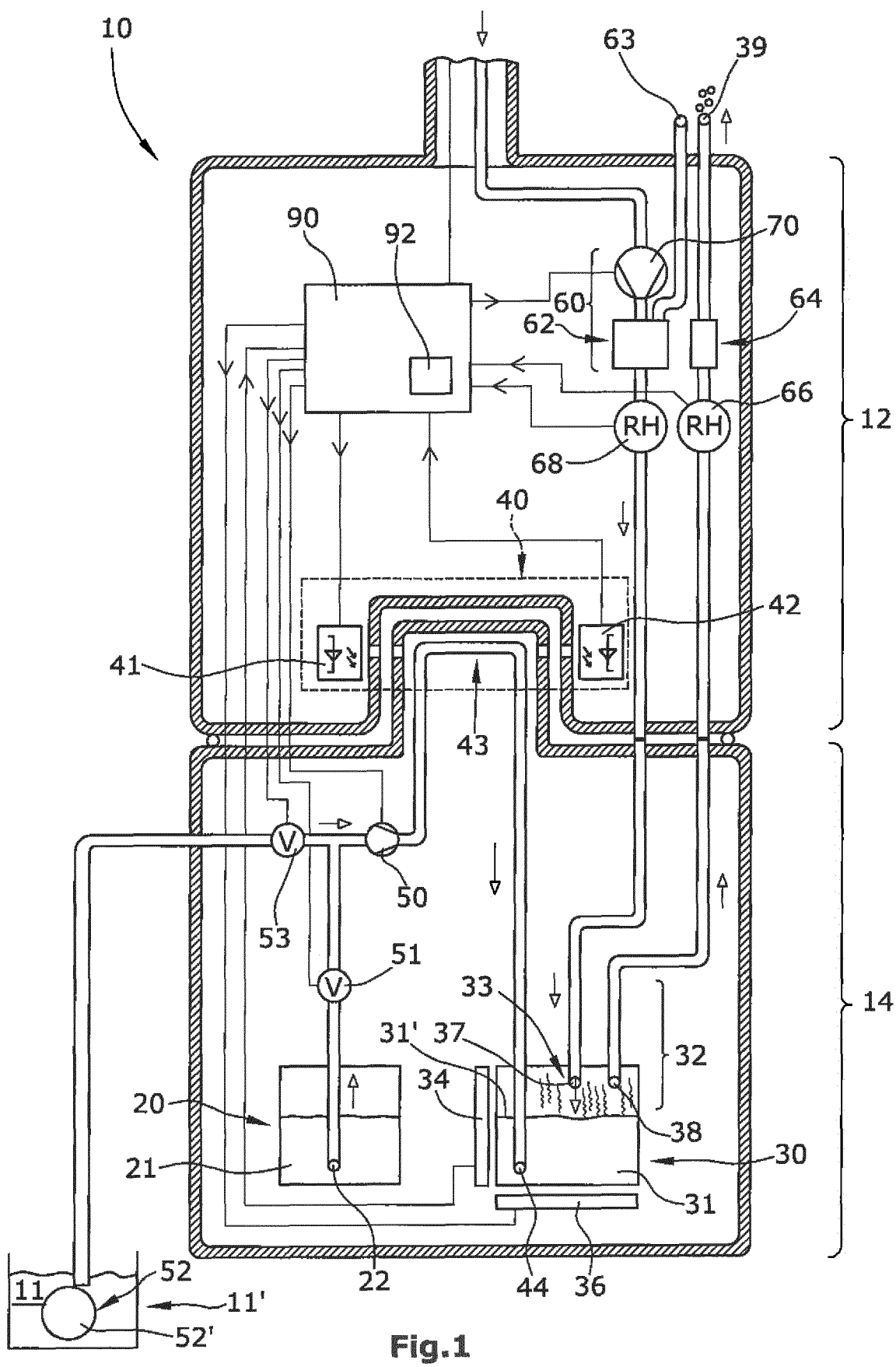

(51) Int. Cl.
  B01L 3/00    (2006.01)
  G01N 31/22    (2006.01)
  B01D 1/14    (2006.01)
  C02F 1/04    (2006.01)
  *G01N 33/18*    (2006.01)
  *G01N 35/10*    (2006.01)

(52) U.S. Cl.
  CPC ......... G01N 21/8507 (2013.01); G01N 31/22 (2013.01); *B01L 3/5027* (2013.01); *G01N 33/18* (2013.01); *G01N 35/1095* (2013.01)

(56) References Cited

U.S. PATENT DOCUMENTS

| | | | | |
|---|---|---|---|---|
| 4,985,118 | A * | 1/1991 | Kurematsu | B01D 1/0082 159/16.1 |
| 5,004,522 | A * | 4/1991 | Koboshi | G03C 5/3952 159/29 |
| 5,207,869 | A | 5/1993 | Harmoning et al. | |
| 5,445,714 | A | 8/1995 | Myers | |
| 8,881,580 | B2 * | 11/2014 | Lundgreen | G01N 35/1095 73/61.41 |
| 2008/0275653 | A1 * | 11/2008 | Cypes | B01D 3/065 702/24 |
| 2011/0207621 | A1 * | 8/2011 | Montagu | B01L 3/502784 506/9 |
| 2012/0167673 | A1 * | 7/2012 | Farjam | F04B 43/12 73/64.56 |
| 2015/0251129 | A1 * | 9/2015 | Heirman | B01D 53/14 95/94 |

* cited by examiner

MICROFLUIDIC PROCESS WATER ANALYZER

The present invention provides a microfluidic process water analyzer as used in the field of water analysis.

A process water analyzer performs a quasi-continuous quantitative determination of an analyte in water, for example for controlling a cleaning process of waste water. The process water analyzer is provided with an optical sensor unit for measuring an optical parameter of the liquid sample and is provided with one or more reagent tanks containing a liquid reagent. The reagent causes a colorimetric reaction with the analyte in the water sample so that the analyte concentration in the water sample can be determined with the optical sensor unit.

Conventional process water analyzers generate up to 50 to 100 l waste liquid per month. The amount of waste liquid can be reduced with microfluidic devices.

US 2011 097 245 A1 discloses a microfluidic analyzer using a cartridge system comprising a cartridge with a reagent tank.

US 2010 0068 723 A1 discloses another microfluidic analyzer using a cartridge concept and including a waste tank.

US 2016 0037 791 A1 discloses another microfluidic analyzer comprising a waste segregation means for separating more hazardous waste from less hazardous waste and comprising waste tanks for different waste categories.

A microfluidic process analyzer significantly reduces the amount of waste liquid but the total amount of liquids, namely remaining reagent liquids and waste liquid, still is several liters per month which is too much to be allowable for shipping with conventional shipping and parcel services.

It is an object of the invention to provide a microfluidic process analyzer generating a minimum amount of waste liquid.

This object of the invention is realized with a microfluidic process analyzer with the features of claim 1.

The microfluidic process analyzer is provided with an analyzer sample inlet through which the liquid sample is pumped to an optical sensor unit for measuring an optical parameter of the liquid sample. The water analyzer is also provided with a reagent tank which is arranged fluidically upstream of the optical sensor unit and which comprises a liquid reagent. The liquid reagent reacts with the liquid sample analyte in a colorimetric manner so that the concentration of the analyte in the liquid sample can finally be measured by the optical sensor unit by an extinction or transmission measurement.

The process water analyzer is also provided with a waste tank which is arranged fluidically downstream of the optical sensor unit. After the liquid sample has been analyzed in the optical sensor unit, the liquid sample is pumped to the waste tank. The waste liquid is not dumped to the environment.

According to the invention, an evaporation arrangement is provided comprising an evaporation chamber arranged fluidically downstream of the optical sensor unit. The evaporation chamber is actively vented with a drying gas pumped from a drying gas source into the evaporation chamber. After the liquid sample has left the optical sensor unit, the liquid sample which is now a "waste liquid" is pumped to the evaporation chamber which can be a separate chamber but alternatively can be defined by the waste tank. In the evaporation chamber, the waste liquid is exposed to a drying gas flow which is directed into the evaporation chamber. The drying gas preferably is dry air and causes evaporation of the waste liquid so that the volume of waste liquid can significantly be reduced.

A typical microfluidic process analyzer will typically generate 2.0 l or more of gross waste liquid leaving the optical sensor unit per month. This gross waste liquid is a mixture of approximately ¼ reagent and ¾ sample liquid. With the evaporation arrangement the volume of waste liquid can be reduced significantly, for example by 75%, so that the final volume of waste liquid is only a fraction of the gross volume of waste liquid.

The use of evaporation for a significant reduction of the final waste liquid volume is a relatively inexpensive and reliable way to finally make it possible to use conventional shipping and parcel services for sending the remaining final volume of waste liquid back to the supplier or to use public waste systems.

According to a preferred embodiment of the invention, the evaporation arrangement is provided with a balancing device for controlling the evaporation activity to keep the total liquid quantity in all tanks substantially equal. The balancing device preferably is a part of the analyzer control unit which controls all sensors and devices of the water analyzer.

The balancing device controls the evaporation activity to keep the total amount of all liquids in the analyzer, namely in all reagent tanks and in all waste tanks, at a constant level. Basically, the evaporation arrangement is controlled so as to evaporate the complete volume of the water liquid samples. As a result, the remaining final waste liquid volume is more or less equal to the used reagent volume, and the concentration of the reagent in the waste tank is not higher than the concentration of the reagent in the reagent tank. Since the final reagent concentration in the waste tank is not higher than in the reagent tank, the final waste liquid is ecologically and legally not more critical than the reagent liquid. As a result, the used tanks can be shipped with the same shipping category as the non-used tanks.

Preferably, the waste tank is provided with a liquid level detector. The liquid level detector allows to determine the total liquid volume in the waste tank so that the result of the evaporation activity can be determined and controlled. The liquid level detector can be the only measure to control the evaporation activity, or can be an additional measure to provide more redundancy for precise control of the evaporation process.

According to a preferred embodiment of the invention, a first humidity sensor is provided in the drying gas path fluidically upstream of the evaporation chamber and a second humidity sensor is provided in the gas path fluidically downstream of the evaporation chamber. With the two humidity sensors, the difference of gas humidity of the drying gas before and after the evaporation chamber can be measured and determined so that the total amount of waste liquid which has been evaporated in the evaporation chamber and has been taken away can be determined.

Preferably, a static base unit and an exchangeable disposable unit are provided which together define the microfluidic process analyzer. The complete liquid fluidics including all tanks is provided in the disposable unit. The disposable unit is one single part which includes and handles all the liquids of the analyzer. The disposable unit is easily exchangeable at the static base unit which basically comprises the analyzer control unit and the optical sensor unit. The static base unit also can comprise parts of the evaporation circuit, in particular parts of the drying gas preparation section upstream of the evaporation chamber.

According to a preferred embodiment of the invention, the evaporation chamber is defined by the waste tank itself. No separate evaporation chamber is provided but the interior of the waste tank is defining the evaporation chamber. This configuration allows to directly control the effect of the evaporation activity in the waste tank because the total final volume of the waste liquid can directly be determined.

Preferably, the evaporation chamber is provided with a drying gas inlet opening at the top region of the evaporation chamber above the maximum or highest possible liquid level. The surface of the waste liquid is vented with the drying gas so that waste liquid water directly can evaporate at the liquid surface into the drying gas flowing by the liquid surface.

Alternatively, the evaporation chamber is provided with a drying gas inlet opening at the bottom region of the evaporation chamber so that the drying gas inlet opening of the evaporation chamber is always below the waste liquid level as soon as a minimum volume of waste water is present in the evaporation chamber. The drying gas s flowing through the waste liquid as gas bubbles and thereby absorbs humidity from the waste liquid. This evaporation method can be more effective than simply directing a drying gas stream to the liquid surface.

According to a preferred embodiment, the drying gas outlet opening of the evaporation chamber is provided and arranged above the maximum liquid level so that it is avoided that waste liquid is pumped through the drying gas outlet path to the outside.

Preferably, a gas drying unit is provided being arranged fluidically upstream of the evaporation chamber. The gas drying unit dries the drying gas before the drying gas enters the evaporation chamber. Preferably, the drying gas is environmental air which is dried down to a relative humidity of 5% to 30%. The dried drying air or drying gas significantly improves the evaporation performance in the evaporation chamber.

According to a preferred embodiment of the invention, the drying gas drying unit is an overpressure membrane dryer. The membrane dryer is provided with a membrane which is transmissive for gaseous water molecules but is not transmissive for non-water molecules. The non-dried gas/air is pumped to the membrane dryer with an overpressure of, for example, more than 2 bar so that gaseous water molecules are forced through the membrane to the low pressure side of the membrane from where the resulting evaporated gas is pumped back into the environment. A membrane drying unit is relatively effective and is an energy economic solution.

Alternatively, the gas drying unit can be a pressure swing absorption device. A pressure swing absorption device is provided with a humidity absorbance unit containing a humidity absorbance substance, as for example molsieve. The pressure swing absorption device works not continuously but in two alternating phases, namely a gas drying phase and absorbance unit drying phase. In the gas drying phase, the incoming gas is flowing through the absorbance unit with relatively high pressure, for example with an overpressure of 1-3 bar, so that the drying gas is dried by the absorbance substance. As soon as the absorbance substance is overloaded with humidity, the gas drying phase is finished and the absorbance unit is dried by gas/air of relatively low pressure flowing through the absorbance unit and then to the environment. For a pressure swing absorption device relatively low overpressures are sufficient to provide the drying process for the drying gas.

According to a preferred embodiment of the invention, an evaporation chamber heating is provided for heating the waste liquid in the evaporation chamber. The warmer the waste liquid is the more water evaporates from the waste liquid into the drying gas. Additionally, the warmer the waste liquid is, the warmer is also the drying gas flowing through the evaporation chamber. And the warmer the drying gas is the higher is the absolute amount of humidity which can be absorbed by the drying gas. In other words, the warmer the waste liquid is, the more effective is the evaporation process.

Preferably, the total volume of all the reagent tanks together is substantially the same as the total volume of all waste tanks together. The evaporation process at the evaporation chamber is controlled so as to keep the total liquid volume more or less constant over the entire use period. As a consequence, the total volume of the waste tanks can be the same as the total volume of the reagent tanks.

According to a preferred embodiment, numerous reagent tanks and numerous waste tanks are provided. All reagent tanks have substantially the same volume and all waste tanks have substantially the same volume. More preferably, the volume of each of all waste tanks is substantially the same as the volume of each of the reagent tanks. The total volume of one single waste tank or reagent tank can be, for example, 250 ml or less. However, the total volume of each of the tanks should allow to use conventional shipping and postal services for delivering the tanks.

The enclosed drawings show some embodiments of the invention.

Figure 2:
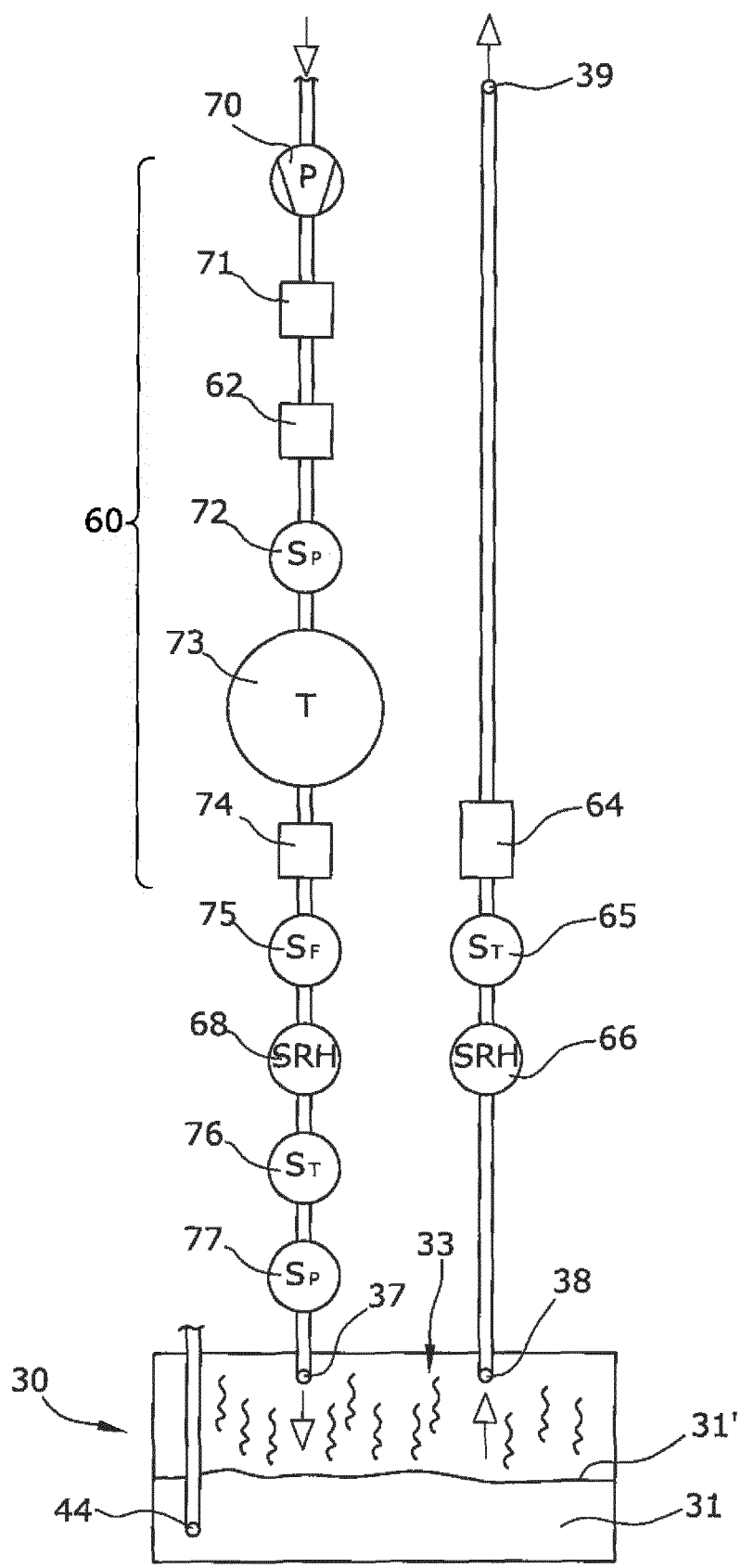
Figure 3:
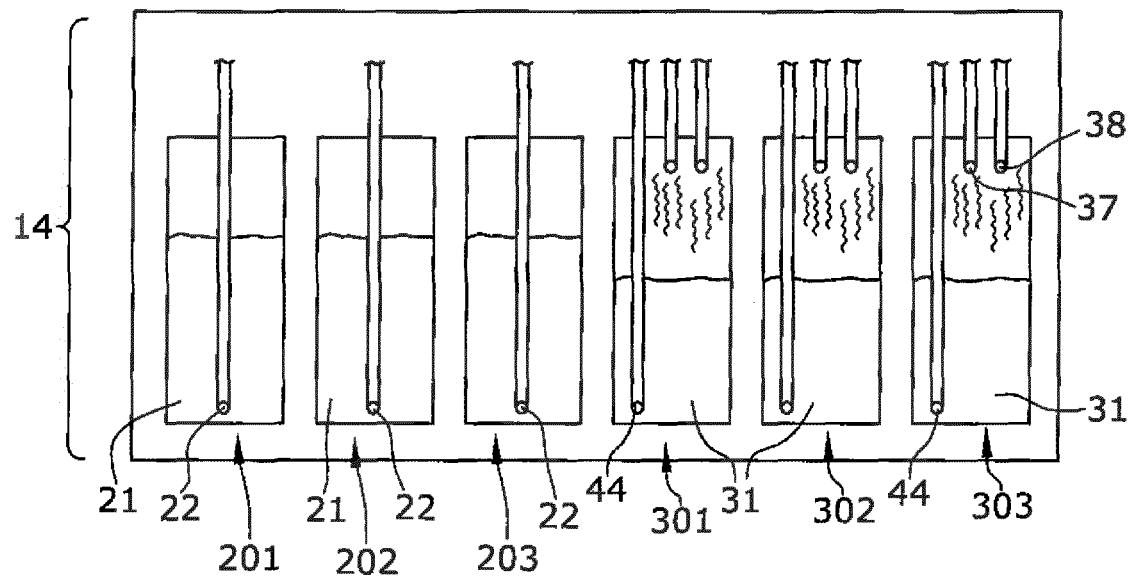
Figure 4A:
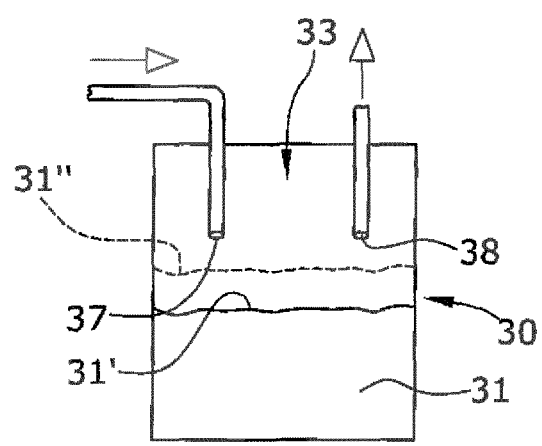
Figure 4B:
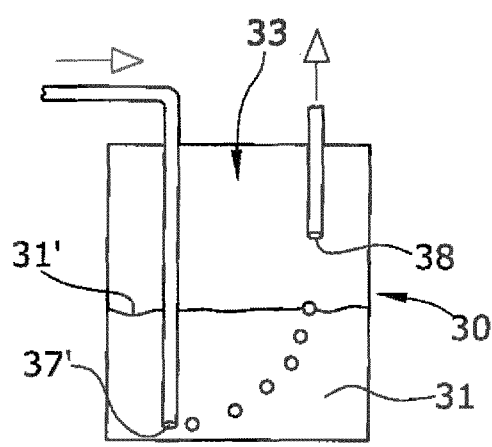
Figures 4C, 4D:
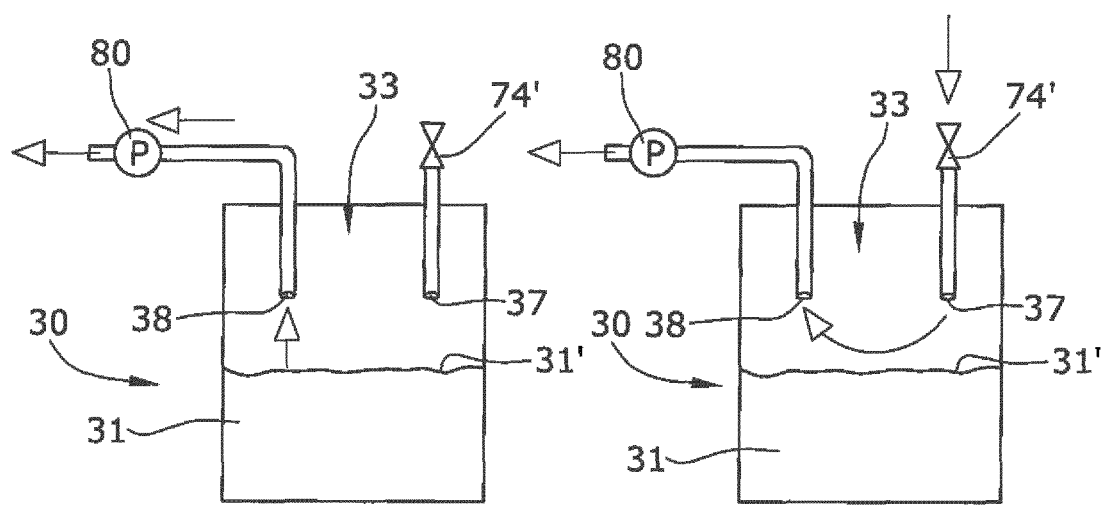
Figure 5:
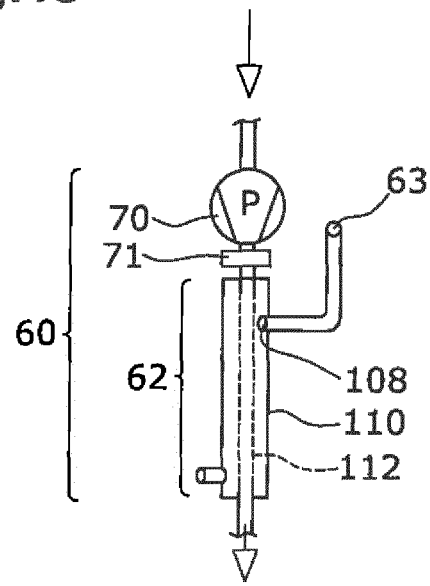
Figure 6:
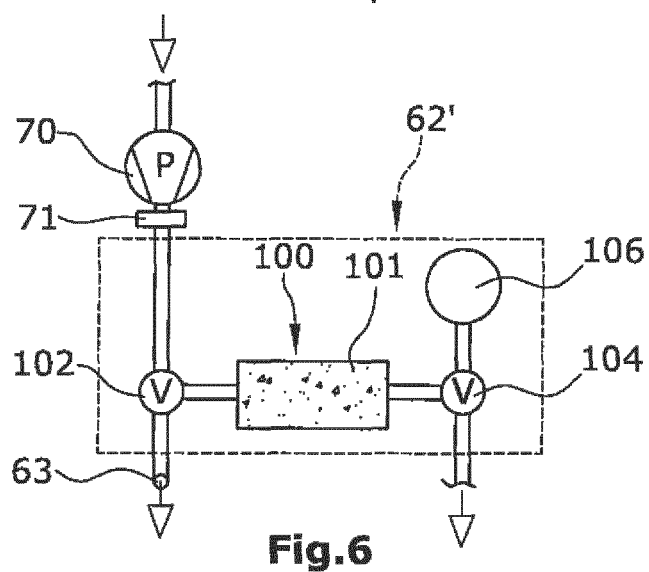

FIG. 1 shows schematically a microfluidic process water analyzer,

FIG. 2 shows schematically the complete gas path of the drying gas of the process water analyzer of FIG. 1, FIG. 3 shows a another embodiment of a disposable unit of the microfluidic process analyzer of FIG. 1, FIGS. 4A to 4D show different embodiments of an evaporation chamber of the process water analyzer of FIG. 1, FIG. 5 shows a first embodiment of a gas drying unit realized as a membrane dryer of the process water analyzer FIG. 1, and FIG. 6 shows a second embodiment of the gas drying unit realized as a pressure swing absorption device of the process water analyzer of FIG. 1.

FIG. 1 shows schematically a microfluidic process water analyzer 10 for continuously controlling the concentration of a selected analyte in water 11, for example in wastewater in a wastewater treatment plant. The water analyzer 10 is designed as a laud-sided device but can, alternatively, be provided as an immersion device. The term 'microfluidic' in this context means that the cross-section of all liquid lines is generally small, preferably smaller than a square millimeters, preferably 1.0 mm².

The water analyzer 10 basically consists of two units, namely a static base unit 12 and an exchangeable disposable unit 14 which is, in use, mechanically, pneumatically and electrically coupled to the base unit 12.

The static base unit 12 is held in position by a stiff support structure at the edge of a water tank 11 comprising water 11. The disposable unit 14 comprises all liquids and all liquid lines of the water analyzer 10.

The disposable unit 14 is provided with an analyzer sample inlet 52 through which a liquid sample is pumped by a sample pump 50 through a sample line and via a sample valve 53 to an optical measuring section 43, and from the optical measuring section 43 finally is pumped to a waste tank 30. The sample inlet 52 is a sample probe immersed into the water 11 of the water tank 11 and is provided with an inlet filter 52! The disposable unit 14 is also provided with a reagent tank 20 with a liquid reagent 21. The liquid reagent 21 is pumped from the reagent tank 20 through a reagent inlet 22 via a reagent valve 51 to the sample line, and leads into the sample line fluidically between the sample valve 33 and the sample pump 50. The liquid sample and the reagent are mixed in a defined mix ratio of, for example 3:1, by alternatively opening and closing the sample valve 53 and the reagent valve 51. The valves 51, 53 and the pump 50 can be driven pneumatically or electrically.

The reagent 21 reacts with the analyte of the liquid sample and thereby causes a colorimetric reaction of the liquid sample. This colorimetric reaction allows to determine the quantity of the analyte in the liquid sample by means of an optical sensor unit 40 which is, in this embodiment, a photometer which measures the transmission or the extinction of the sample liquid flowing through the optic measuring section 43.

The electric components of the optical sensor unit are provided in the base unit 12 and basically are a light emitter 41 and a light sensor 42. The optical measuring section 43 of the sample line is axially aligned and in-line with the light emitter 41 and the light sensor 42. Downstream of the liquid line measuring section 43 the liquid line leads to a waste liquid outlet 44 within the waste tank 30 so that waste liquid 31 is accumulated in the waste tank 30.

The disposable unit 14 is provided with an evaporation arrangement 32 which is substantially defined by a drying gas inlet opening 37 within the waste tank 30, a drying gas outlet opening 38 within the waste tank 30 and an evaporation chamber 33 defined by the waste tank 30 itself so that no separate vessel for the evaporation chamber is provided. The drying gas inlet opening 37 is provided at the top region of the evaporation chamber 33 above the possible maximum level 31" of the waste liquid 31, as shown in FIG. 4A. Alternatively, the drying gas inlet opening 37' can be provided at the bottom region of the evaporation chamber 30 as shown in FIG. 4B so that the drying gas inlet opening 37' is always below the liquid level 31' if a minimum volume of waste liquid 31 is accumulated in the waste tank 30. The drying gas outlet opening 38 is provided at the top region of the waste tank 30 above the maximum liquid level 31".

The waste tank 30 is provided with a waste tank heating 36 for heating the waste tank 30 and, in particular, for heating the waste liquid 31. The waste tank heating 36 can be provided with a temperature sensor for controlling the temperature of the waste liquid 31 so that the waste liquid 31 has a constant liquid temperature. The waste tank 30 is also provided with a liquid level detector 34 for exactly detecting the liquid level 31' of the waste liquid 31. The liquid level detector 34 and the waste tank heating 36 are preferably provided as parts of the base unit 12 to keep the costs for the disposable unit low.

The evaporation arrangement 32 is supplied with a drying gas coming from a drying gas source 60 which is provided in the base unit 12. The complete path of the drying gas is schematically shown in FIG. 2. The drying gas which is environmental air is sucked and pumped into the drying gas path by a drying gas pump 70. The drying gas path downstream of the pump 70 is provided with a condensate trap 71, a gas drying unit 62, a first pressure sensor 72 and a gas tank 73. The condensate trap 71 separates condensate from the drying gas flowing through. The gas drying unit 62 actively dries the drying gas as described below with reference to FIGS. 5 and 6. The first pressure sensor 72 detects the static pressure of the pumped drying gas.

A control valve 74, a flow sensor 75, a first humidity sensor 68, a first temperature sensor 76 and a second pressure sensor 77 are provided downstream of the gas tank 73 and fluidically before the evaporation chamber 33. The flow control valve 74 detects the gas flow between the gas tank 73 and the evaporation chamber 33. The humidity sensor 68 detects the relative humidity RH, the first temperature sensor 76 detects the temperature and the second pressure sensor 77 detects the static pressure of the drying gas in the drying gas path between the gas tank 73 and the evaporation chamber 33.

A second humidity sensor 66, a second temperature sensor 65 and an outlet filter 64 are provided in the gas path downstream of the evaporation chamber 33. The gas path finally ends at an analyzer gas outlet 39 outside the housing of the base unit 12.

The outlet filter 64 can be an activated carbon filter and is provided for absorbing volatile components of the reagent, such as, for example, formaldehyde and chlorine vapors.

All sensors, the light emitter 41, the waste tank heating 36 and other electric devices of the water analyzer 10 are connected to a control unit 90 by signal lines or control lines. The digital control unit 90 is provided with a digital balancing device 92 which keeps the total volume of liquid within the water analyzer 10, and in particular within the disposable unit 14 basically constant. In particular, the sum of the volume of liquid reagent 21 in the reagent tank 20 and the volume of waste liquid 31 in the waste tank 30 is kept constant.

The sample pump 50 is a volumetric pump so that the amount of reagent 21 and sample liquid pumped by the sample pump 50 is exactly known to the balancing device 92. From the measured values of the five sensors 68, 74-77 between the gas tank 73 and the evaporation chamber 33 the balancing device 92 knows the exact condition and volume of the drying gas entering the evaporation chamber 33 through the drying gas inlet opening 37. The second humidity sensor 66 and the second temperature sensor 65 downstream of the evaporation chamber 33 allow the balancing device 92 to calculate the amount of water humidity which has been absorbed by the drying gas in the evaporation chamber 33. The balancing device 92 calculates on the basis of this information how much liquid water has been absorbed in the evaporation chamber in form of humidity.

The evaporation process is stopped as soon as the balancing device 92 determines that the total volume of sample liquid sucked in has been evaporated at and by the evaporation arrangement 32. The balancing device 92 keeps the total amount of liquid in the disposable unit 14 of the water analyzer 10 constant.

FIG. 3 shows a more sophisticated embodiment of the arrangement of the tanks. The disposable unit 14 is provided with three reagent tanks 201, 202, 203 and with three waste tanks 301, 302, 303, whereas the volume of each of all tanks 201, 202, 203, 301, 302, 303 is equal, and can be, for example, 250 ml for each of all tanks. As a result, also the total volume of all reagent tanks 201, 202, 203 together and the total volume of all waste tanks 301, 302, 303 is equal, namely 750 ml.

In the two embodiments shown in FIGS. 4A and 4B, a continuous evaporation process is realized. FIGS. 4C and 4D show two phases of a discontinuous evaporation process in a third embodiment. As shown in FIGS. 4C and 4D, a flow valve 74' is provided in the inlet path which is closed in a first process step and thereby does not allow drying gas to flow into the evaporation chamber 33 as shown in FIG. 4C. A suction pump 80 in the outlet path is always activated and generates a vacuum within the evaporation chamber 33 so that an increased mass of water humidity vaporizes and evaporates and is sucked through the drying gas outlet opening 38 to the environment. As soon as a set negative pressure is achieved, the valve 74' opens in a second process step into the evaporation chamber 33. As soon as atmospheric pressure is achieved within the evaporation chamber 33, the flow control valve 74' is closed again, and the process continues with the first step.

FIG. 5 shows a first embodiment of a gas drying unit 62 which is an overpressure membrane dryer. The gas drying unit 62 is provided with a tubular membrane 112 surrounded by a gas-tight tubular housing 110. The membrane 112 is transmissive for water molecules but is not transmissive for other molecules of the air flowing through the gas drying unit 62. The ringlike space around the tubular membrane 112 is vented by a venting gas which flows out of the drying unit housing 110 to a drying unit condensate outlet 63. The drying gas is pumped by the drying gas pump 70 with an overpressure of 1 to 3 bar into the drying gas unit 62 so that the drying gas flowing through is effectively dried.

FIG. 6 shows a second embodiment of a gas drying unit 62' which is realized as a pressure swing absorption device. In the charging step, the drying gas is pumped by the drying gas pump 70 through a first switch 102 through an humidity absorption unit 100 and via a second switch 104 into the drying gas path downstream of the gas drying unit 62'. The humidity absorption unit 62' contains a filling of a humidity absorbent substance 101 which is continuously charged with humidity. As soon as the humidity absorbent substance 101 is saturated with humidity, the switch valves 102, 104 are switched so that the discharge step is started and a pump tank 106 which is filled with dried pressurized gas generates a gas flow from the pump tank 106 through the humidity absorbance unit 100 to the drying unit condensate outlet 63, so that the absorption unit is discharged after a while. Then the following charging step is stated by reswitching the valves 102, 104.

The gas drying unit can alternatively be provided as a peltier-dryer or as an air-water separator using an overpressure of, for example, 3 bar to extract humidity from the air.

The invention claimed is:

1. A microfluidic process water analyzer comprising:
   an analyzer sample inlet,
   an optical sensor unit for determination of an optical parameter of a liquid sample,
   a reagent tank being arranged fluidically upstream of the optical sensor unit and comprising a liquid reagent,
   a waste tank fluidically downstream of the optical sensor unit,
   a sample pump co-located with the reagent tank and the waste tank within a module,
   an evaporation arrangement comprising an evaporation chamber arranged fluidically downstream of the optical sensor unit, the evaporation chamber being actively vented with a drying gas pumped from a gas source to the evaporation chamber, wherein the drying gas absorbs humidity from the evaporation chamber with the humidity actively vented from the microfluidic process water analyzer, wherein the evaporation arrangement is provided with a balancing device to maintain liquid quantity such that a final waste volume in the waste tank is similar to a volume of the liquid reagent.

2. The micro fluidic process analyzer of claim 1, wherein the waste is provided with a liquid level detector.

3. The microfluidic process analyzer of claim 1, wherein a first humidity sensor is provided in the drying gas path fluidically upstream of the evaporation chamber and a second humidity sensor is provided in the gas path fluidically downstream of the evaporation chamber.

4. The microfluidic process analyzer of claim 1, wherein a static base unit and an exchangeable disposable unit are provided, the complete liquid fluidics including the tanks being provided in the disposable unit.

5. The microfluidic process analyzer of claim 1, wherein the evaporation chamber is defined by the waste tank.

6. The microfluidic process analyzer of claim 1, wherein the evaporation chamber is provided with a drying gas inlet opening at the top region of the evaporation chamber above the maximum liquid level.

7. The microfluidic process analyzer of claim 1, wherein the evaporation chamber is provided with a drying gas inlet opening at the bottom region of the evaporation chamber.

8. The microfluidic process analyzer of claim 1, wherein the evaporation chamber is provided with a drying gas outlet opening above the maximum liquid level.

9. The microfluidic process analyzer of claim 1, wherein a gas drying unit is provided which is arranged fluidically upstream of the evaporation chamber.

10. The microfluidic process analyzer of claim 9, wherein the gas drying unit is an over pressure membrane dryer.

11. The microfluidic process analyzer of claim 9, wherein the gas drying unit is a pressure swing absorption device.

12. The microfluidic process analyzer of claim 9, wherein the gas drying unit is a passive device comprising a humidity absorbent substance.

13. The microfluidic process analyzer of claim 1, wherein an evaporation chamber heating is provided for heating the waste liquid in the evaporation chamber.

14. The microfluidic process analyzer of claim 1, wherein the total volume of all reagent tanks is substantially the same as the total volume of all waste tanks.

15. The microfluidic process analyzer of claim 1, wherein numerous reagent tanks and numerous waste tanks are provided, all reagent tanks having substantially the same volume and all waste having substantially the same volume.

* * * * *